United States Patent [19]

Young et al.

[11] Patent Number: 5,569,284
[45] Date of Patent: Oct. 29, 1996

[54] MORCELLATOR

[75] Inventors: Wayne P. Young, Brewster, N.Y.;
Darryl S. Pereira, Monroe, Conn.;
Salvatore Castro, Seymour, Conn.;
Michael S. Kolesa, Norwalk, Conn.;
Dominick L. Mastri, Bridgeport,
Conn.; Frank J. Viola, Sandy Hook,
Conn.

[73] Assignee: United States Surgical Corporation, Norwalk, Conn.

[21] Appl. No.: 311,395

[22] Filed: Sep. 23, 1994

[51] Int. Cl.$^6$ ............................ A61B 17/14; A61B 17/32
[52] U.S. Cl. ............................ 606/180; 606/170; 604/22
[58] Field of Search ............................ 606/167, 168, 606/170, 171, 180, 127, 185, 79, 80, 128; 128/749, 751, 752

[56] References Cited

U.S. PATENT DOCUMENTS

| | | |
|---|---|---|
| 2,540,936 | 2/1951 | Daniels . |
| 4,111,207 | 9/1978 | Seiler, Jr. . |
| 4,282,884 | 8/1981 | Boebel . |
| 4,428,375 | 1/1984 | Ellman . |
| 4,589,414 | 5/1986 | Yoshida et al. . |
| 4,649,919 | 3/1987 | Thimsen et al. . |
| 4,651,753 | 3/1987 | Lifton . |
| 4,830,000 | 5/1989 | Shutt . |
| 4,844,064 | 7/1989 | Thimsen et al. . |
| 4,850,354 | 7/1989 | McGurk-Burleson et al. . |
| 4,867,157 | 9/1989 | McGurk-Burleson et al. . |
| 4,936,313 | 6/1990 | Burkhardt et al. . |
| 4,994,024 | 2/1991 | Falk . |
| 5,007,917 | 4/1991 | Evans . |
| 5,084,052 | 1/1992 | Jacobs . |
| 5,106,364 | 4/1992 | Hayafuji et al. . |
| 5,176,687 | 1/1993 | Hasson et al. . |
| 5,176,695 | 1/1993 | Dulebohn . |
| 5,190,561 | 3/1993 | Graber . |
| 5,195,954 | 3/1993 | Schnepp-Pesch et al. . |
| 5,207,697 | 5/1993 | Carusillo et al. . |
| 5,215,521 | 6/1993 | Cochran et al. . |
| 5,217,479 | 6/1993 | Shuler . |
| 5,224,930 | 7/1993 | Spaeth et al. . |
| 5,226,910 | 7/1993 | Kajiyama et al. . |
| 5,234,453 | 8/1993 | Smith et al. .................. 606/170 |
| 5,242,460 | 9/1993 | Klein et al. . |
| 5,269,785 | 12/1993 | Bonutti . |
| 5,275,609 | 1/1994 | Pingleton et al. . |
| 5,281,230 | 1/1994 | Heidmueller . |
| 5,290,303 | 3/1994 | Pingleton et al. . |
| 5,300,087 | 4/1994 | Knoepfler . |
| 5,301,684 | 4/1994 | Ogirala .................. 128/754 |
| 5,304,124 | 4/1994 | Essig et al. . |
| 5,304,181 | 4/1994 | Caspari et al. . |
| 5,318,589 | 6/1994 | Lichtman . |
| 5,320,627 | 6/1994 | Sorensen et al. . |
| 5,324,301 | 6/1994 | Drucker . |
| 5,335,671 | 8/1994 | Clement . |
| 5,439,474 | 8/1995 | Li . |

FOREIGN PATENT DOCUMENTS

| | | |
|---|---|---|
| 621008 | 10/1994 | European Pat. Off. . |
| WO94/15533 | 7/1994 | WIPO . |

OTHER PUBLICATIONS

Cushieri, A. et al., *Slicer and Tissue Retrieval System for Excisional Endoscopic Surgery*, Surgical Endoscopy vol. 8, 1246–1249 (1994).

*Primary Examiner*—Michael Powell Buiz
*Assistant Examiner*—Mark S. Leonardo

[57] ABSTRACT

An endoscopic morcellator includes a tubular portion with an elongated auger rotatably positioned within its bore. An aperture near the distal end of the tubular portion permits access for body tissue to contact the auger. The auger is driven by a reversible motor which is powered by a battery pack. A container collects morcellized tissue which is aspirated by means of a suction tube.

24 Claims, 7 Drawing Sheets

MORCELLATOR

BACKGROUND

1. Technical Field

The subject application relates to a surgical apparatus for fragmenting and removing tissue or bodily organ parts during surgery, and is particularly adapted for use during minimally invasive surgical procedures.

2. Background of Related Art

One of the recent advances in the surgical area has been the development of minimally invasive surgical procedures such as endoscopic and laparoscopic surgery. Minimally invasive surgery reduces patient trauma and speeds recovery time as opposed to more conventional procedures in which a large portion of the patient's body is opened. Generally, endoscopic surgery involves incising through body walls for examining, viewing and/or operating on various bodily organs or structures, including the ovaries, uterus, gall bladder, bowels, kidneys, appendix, etc. In endoscopic procedures, a trocar typically creates an incision and trocar tubes or cannula devices are extended into and left in place in the abdominal wall so that endoscopic surgical tools may be inserted through the trocar cannula. A camera or endoscope is inserted through the trocar cannula which, is generally located at the navel incision, thereby enabling the visual inspection and magnification of a cavity in the body. The surgeon then performs the desired procedure at the surgical site with the aid of specialized instrumentation designed to fit through additional trocar cannulas which provide additional entries into the desired body cavity. Thus, instead of a rather large incision (typically 12 inches or larger) necessary to complete a fully invasive surgical procedure, endoscopic surgery results in several smaller incisions, usually between 5 and 15 millimeters in size. In most instances, recovery is quicker and less painful than traditional surgery. In addition, because the surgical field is greatly magnified surgeons are often better able to dissect blood vessels and control blood loss. In addition, heat and water loss are often reduced as a result of the smaller incisions.

In many surgical procedures, it is often necessary to remove tissue or diseased organs. This is especially challenging during endoscopic surgery because the tissue or organ removal must be achieved through the small openings through which the procedure is performed. In these situations it may be desirable to fragment, or morcellate, or cut into smaller segments the bodily tissue so that it can be readily removed through the small endoscopic openings.

Morcellation involves fragmenting and removing diseased tissue or organ parts from healthy tissue or organs. In endoscopic morcellation, the fragmented pieces are typically removed from the patient's body through a small incision or through a trocar cannula device which extends through the abdominal wall. When the tissue or organ part is diseased or infected, it is preferred that the excised portions thereof be isolated from contact with surrounding healthy tissue. Accordingly, it is often necessary to enclose the fragmented organ during removal, thus preventing contamination of healthy tissue and bodily organs. A device for accomplishing such a task is disclosed in U.S. Pat. No. 4,428,375 which describes a drawstring bag for encapsulating a fragmented organ during surgical repair. In some instances, the organ is fragmented in the bag by a surgical device known as a morcellator, until such a time as the entire specimen is small enough to be removed while in the bag, from the abdominal cavity, via the trocar cannula.

Generally, there are two types of endoscopic morcellators, manually operated and electrically assisted. Manually operated morcellators are typically operated by a hand lever connected to an elongated endoscopic member. The distal end of the endoscopic member is connected to cutting members which are operatively associated through the endoscopic member with the hand lever. In use, the manually operated morcellator is advanced to the surgical site where the tissue or bodily organ part to be separated is positioned between the cutting members. The surgeon then actuates the cutting members to cut the tissue or organ part. If the removal of the tissue or organ is being performed without a surgical bag, the surgeon must repeatedly remove the morcellator completely from the abdominal cavity to remove the fragmented tissue or bodily organ part from the cutting member and then reinsert the morcellator, via the trocar cannula, back to the surgical site to remove a further tissue or organ part. If the removed tissue or organ is diseased or infected, it may be necessary to place the organ in a surgical bag prior to fragmentation and removal. When the surgical bag is employed, the cutting edges of the morcellator cannot cut the surgical bag because such would result in tearing the bag and potentially exposing diseased tissue to healthy body tissue.

Electric morcellators are generally used in conjunction with a surgical bag and are typically provided with a high speed cutting blade that rapidly fragments the tissue or organ into very small pieces within the bag to enhance removability. The fragmented tissue or organ can then be aspirated from the bag, or the entire bag may be removed containing the fragmented tissue. One such electric morcellator is described in U.S. Pat. No. 5,215,521 to Cochran et al.

Such electric morcellators may disadvantageously result in the rotating cutting blade cutting the surgical bag, thus risking the possibility that healthy tissue surrounding the surgical bag may become contaminated by the resulting leakage.

Thus, there exists a need for an endoscopic morcellator which is easy to operate, and capable of removing diseased tissue without tearing or puncturing a surgical removal bag and thereby infecting surrounding healthy tissue.

SUMMARY

Because endoscopic procedures are more common than laparoscopic procedures, the present application utilizes terms of endoscopic procedures and apparatus. However, use herein of terms such as "endoscopic", "endoscopically", and "endoscopic portion", among others, should not be construed as limited to an apparatus for use only in conjunction with an endoscopic tube. To the contrary, it is believed that the apparatus described herein may find use in other minimally invasive surgical procedures wherein access is limited to a small incision, such as, for example, laparoscopic or arthroscopic procedures.

A surgical apparatus is provided herein for morcellizing body tissue, especially in an endoscopic procedure. The surgical apparatus comprises an endoscopic portion including an elongated tubular member having an axial bore, and an elongated auger rotatably disposed within the axial bore, the elongated tubular member having an aperture which provides access for body tissue to contact the auger. A cover member movable between open and closed positions is provided to cover or uncover the access aperture. The apparatus further includes a housing portion releasably engaged with the first portion and having a rotary driver operatively associated with the auger, and an actuation member responsive to user contact for actuating the rotary driver. The rotary driver may be reversed to operate in the opposite rotational direction.

The apparatus further can include a tissue collection container and a suction tube for aspirating tissue and fluids.

Also provided herein is a method for employing the apparatus described herein in an endoscopic surgical procedure.

BRIEF DESCRIPTION OF THE DRAWINGS

Various embodiments are described herein with reference to the drawings wherein.

DETAILED DESCRIPTION OF THE PREFERRED EMBODIMENT(S)

In the drawings and in the description which follows, the term "proximal", as is traditional, will refer to the end of the surgical apparatus which is closest to the operator, while the term "distal" will refer to the end of the apparatus which is furthest from the operator.

Figure 1:
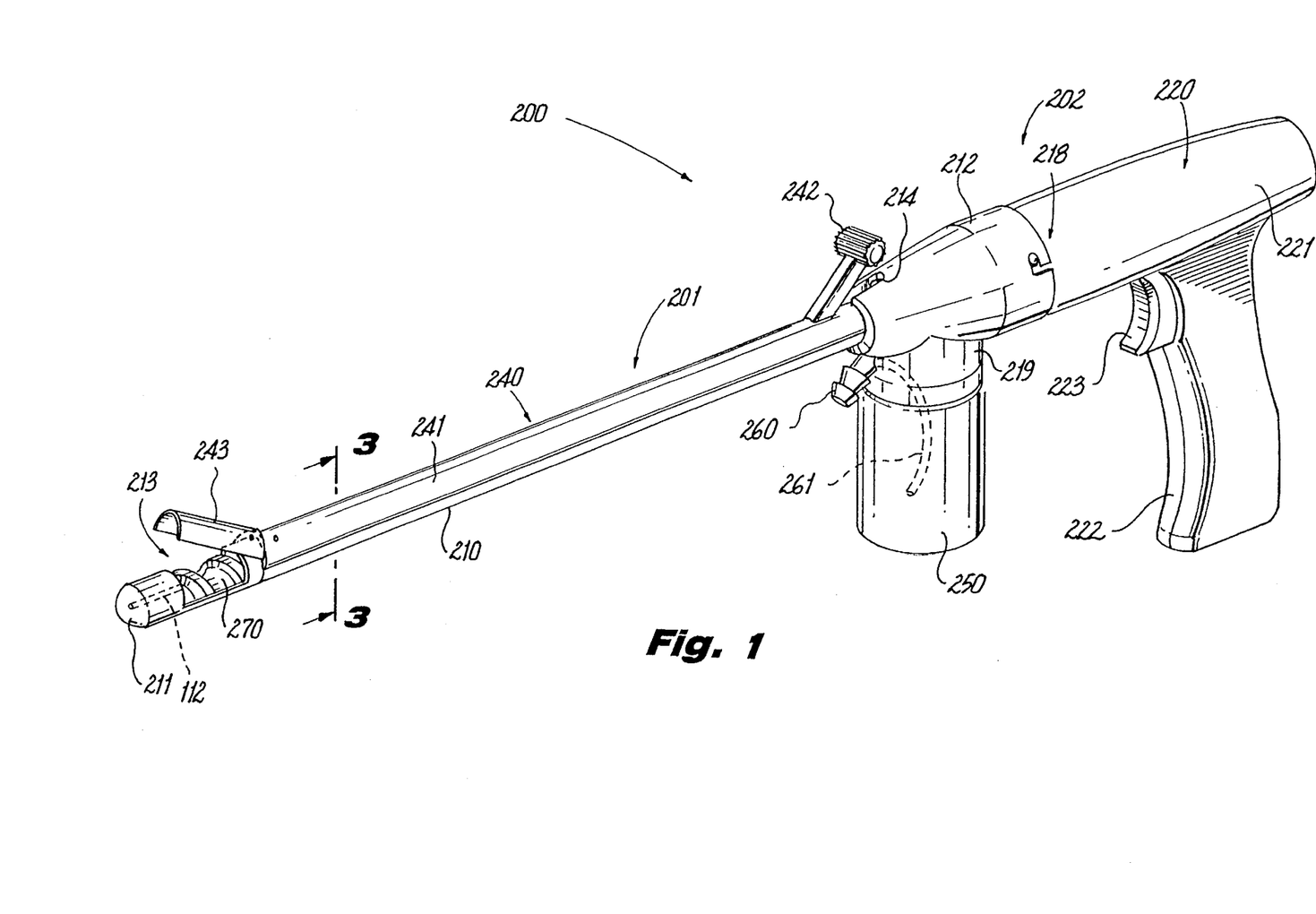
FIG. 1 is a perspective view of an endoscopic morcellator.

Referring to FIG. 1, the endoscopic morcellator apparatus 200 includes an endoscopic portion 201 extending from body portion 212 and a housing portion 202 which is removably attached to the body portion 212. The endoscopic portion 201 and body portion 212 or the housing portion 202 may be detached and replaced if desired. For example, if batteries 253 (FIG. 8) contained in the housing portion 202 run low the housing portion 202 may be detached and replaced. Likewise, if desired, the endoscopic portion 201 and body portion 212 may be detached from housing portion 202 and replaced. Preferably, a bayonet type mounting feature 218 may be used to facilitate such removable attachment. The endoscopic portion 201, the body portion 212, and the housing portion 202 are configured to be disposable after the surgical procedure is completed.

The endoscopic portion 201 includes an elongated tubular member 210 mounted to the body portion 212 by a rotatable coupling. A circumferential flange 203 at the proximal end of the tubular member 210 can be employed to permit rotation of the tubular member 210 while preventing disengagement of the tubular member 210 from the body portion 212. Tubular member 210 has a closed and rounded distal end 211, and an axial bore 115 (FIG. 3) through which a tissue morcellating auger 170 is rotatably disposed.

Figures 2, 3:
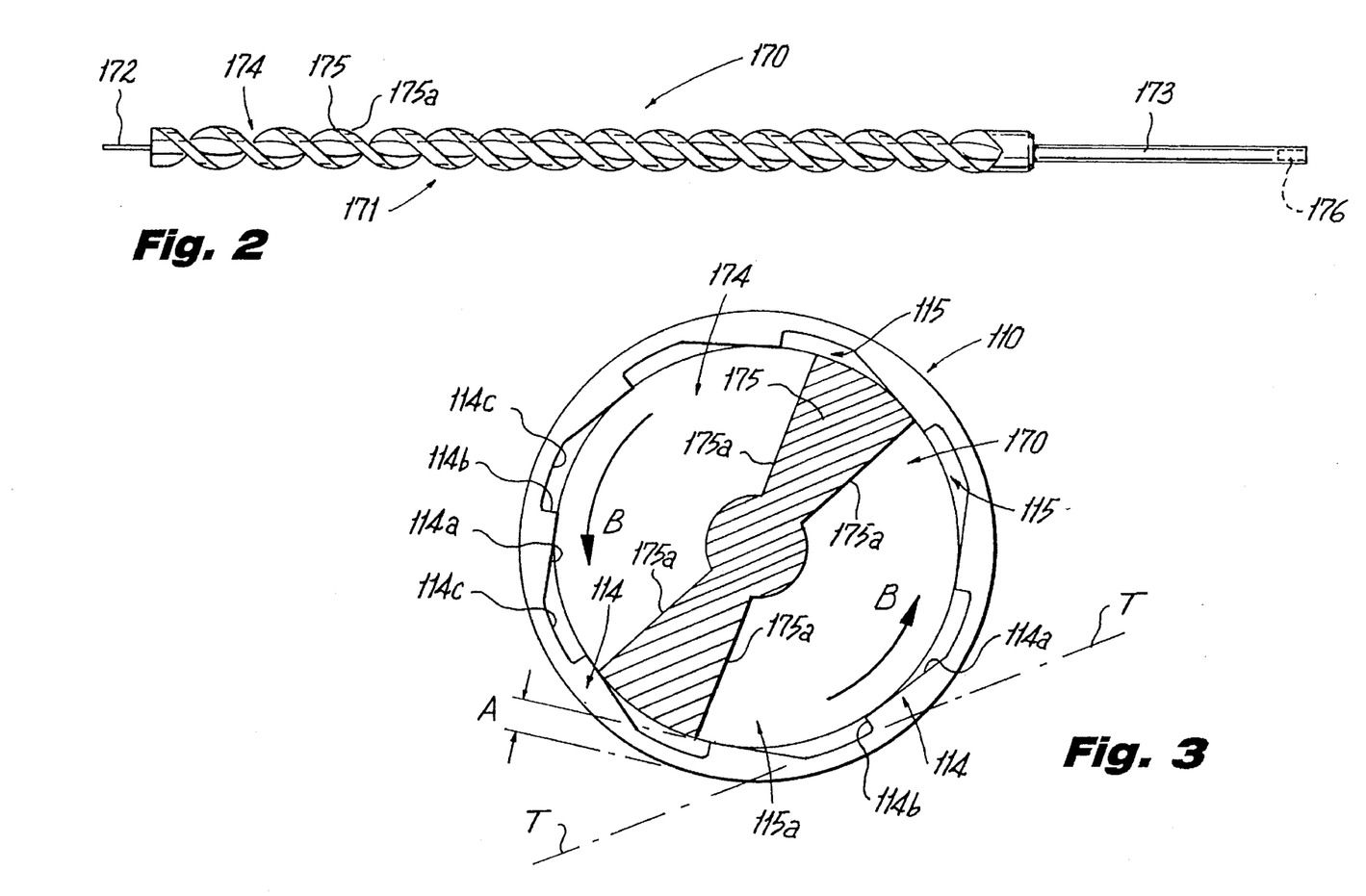
FIG. 2 is a side view of an auger for use in the endoscopic morcellator.
FIG. 3 is a sectional view of the tubular member showing the internal ribs and the auger disposed within the bore of the tubular member.

Referring to FIG. 2, the auger 170 is an elongated member preferably of single piece construction and fabricated from a surgically compatible material such as stainless steel. Alternatively, auger 170 may be fabricated from a suitable plastic capable of withstanding the forces necessary for morcellation. Auger 170 comprises a screw section 171 having a plurality of flutes 174 and lands 175, the lands each having at least one sharp cutting edge 175a. The flutes 174 and lands 175 define a plurality of helical cutting blades for grinding body tissue into small pieces and moving the ground tissue longitudinally through the bore 115 of the tubular member 210 as the auger 170 rotates. The axle 172 is located at the distal end of the auger 170 and is rotatably mounted in a distal aperture 112 (FIG. 1) of the tubular member 210. A proximal shaft portion 173 includes a proximal shaped aperture 176 for engagement with a correspondingly shaped drive shaft 236 (FIG. 7) to enable connection of auger 170 by a transmission to a motor 230 which causes the auger 170 to rotate around a longitudinal axis.

The tubular member 210 includes internal ribs 114 such as are shown in FIG. 3. Referring to FIG. 3, longitudinally extending ribs 114 extend from the inner wall 114c of the tubular member 210 into axial bore 115 and are shaped so as to facilitate the movement of tissue longitudinally through bore 115. Ribs 114 are preferably formed integrally with inner wall 114c, but alternatively may be attached to inner wall 114c by a suitable adhesive. Ribs 114 each have a planar first side 114a which is inclined at an angle "A" with respect to a tangent line "T", which is a tangent to the inner wall 114c at the intersection of the inner wall 114c with the planar side 114a. The ribs 114 also each have a planar second side 114b which is preferably oriented radially with respect to the axial centerline of the tubular member 210. This orientation facilitates clockwise rotation of the auger 170 as depicted by arrows "B". Body tissue cut by lands 175 is drawn up through the space 115a defined by the flutes 174 and is transported longitudinally through region 115b between the auger 170 and the inner wall 114c of the tubular member 210. The body tissue is further morcellated by being ground against side 114a of the ribs 114 as the auger 170 turns.

Referring now to FIG. 1, the elongated tubular member 210 further includes an access aperture 213 spaced from the distal end 211 which permits access to the axial bore 115 and auger 170. Access aperture 213 enables tissue which is external to the tubular member 210 to enter the axial bore 115 and contact auger 170 for morcellation. As stated above, the tubular member 210 is rotatable independently of body portion 212, which enables the access aperture 213 to be reoriented in different lateral directions for reception of body tissue as described in greater detail below.

Figure 4:
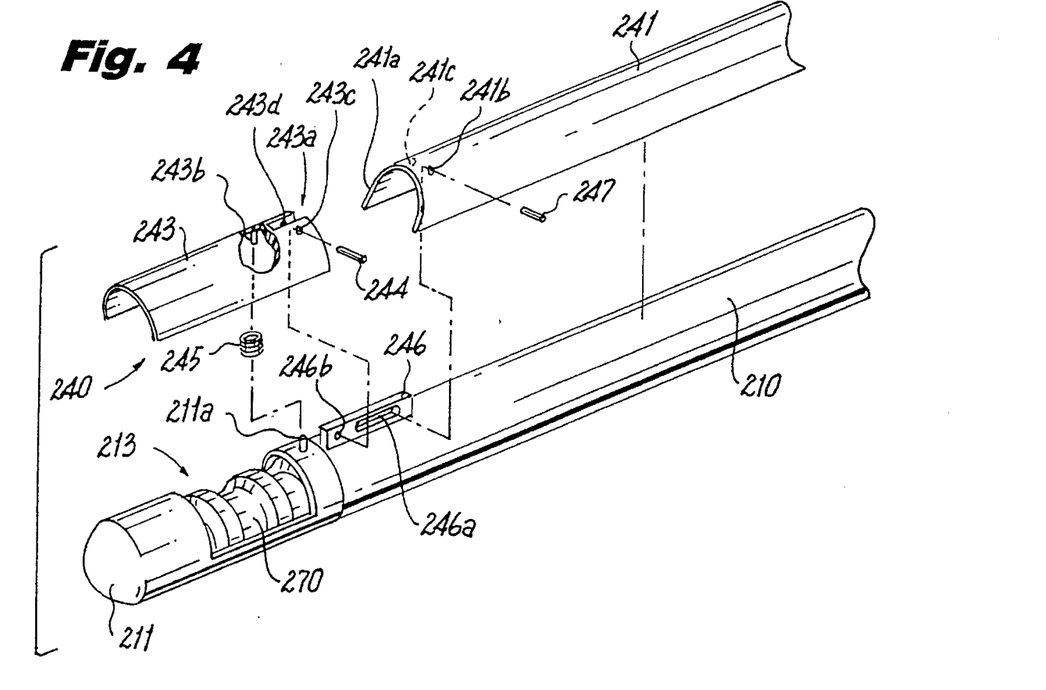
FIGS. 4 to 6 illustrate the hinged cover member and jaw actuator.
Figure 5:
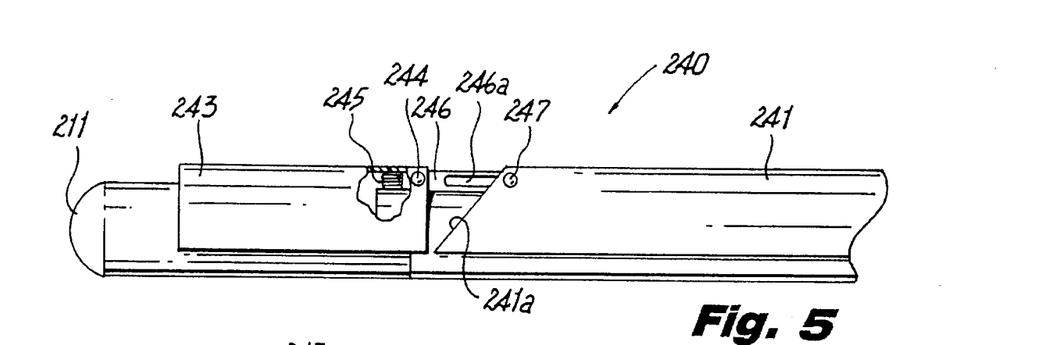
Figure 6:
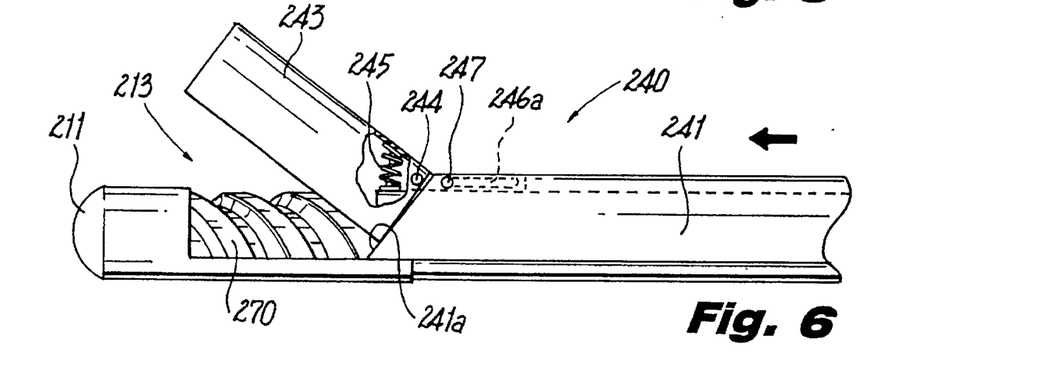

A cover flap 243 which is a jaw pivotally movable between an open position and a closed position to selectively cover and uncover aperture 213 to allow access to auger 170 is additionally shown in FIGS. 4 to 6. In the open position the cover flap 243 provides access for body tissue to enter aperture 213 to contact auger 170 for morcellation thereby. As it moves from the open to the closed position, cover flap 243 applies a force to bias the body tissue to contact the auger 170. In the closed position cover flap 243 prevents the auger 170 from contacting material unintended for morcellation, such as the surgical bag in which the operation is performed.

More particularly, the endoscopic portion 201 of the apparatus 200 includes a tissue engagement and biasing mechanism 240 which includes the cover flap 243 and an elongated partially cylindrical jaw actuator 241 partially disposed within body portion 212 and extending along the elongated tubular member 210 and being in slidable contact therewith. The proximal end portion of the jaw actuator 241 includes an actuator lever 242 (See, FIGS. 1 and 7) attached thereto and positionable within slot 214 disposed on the distal end of the body portion 212 when lever 242 is moved into a retracted proximal position. (FIG. 7) When actuator lever 242 is moved in the distal direction to a forward position out of slot 214 as shown in FIG. 1, it slides jaw actuator 241 distally to a forward position with respect to tubular member 210.

Figure 7:
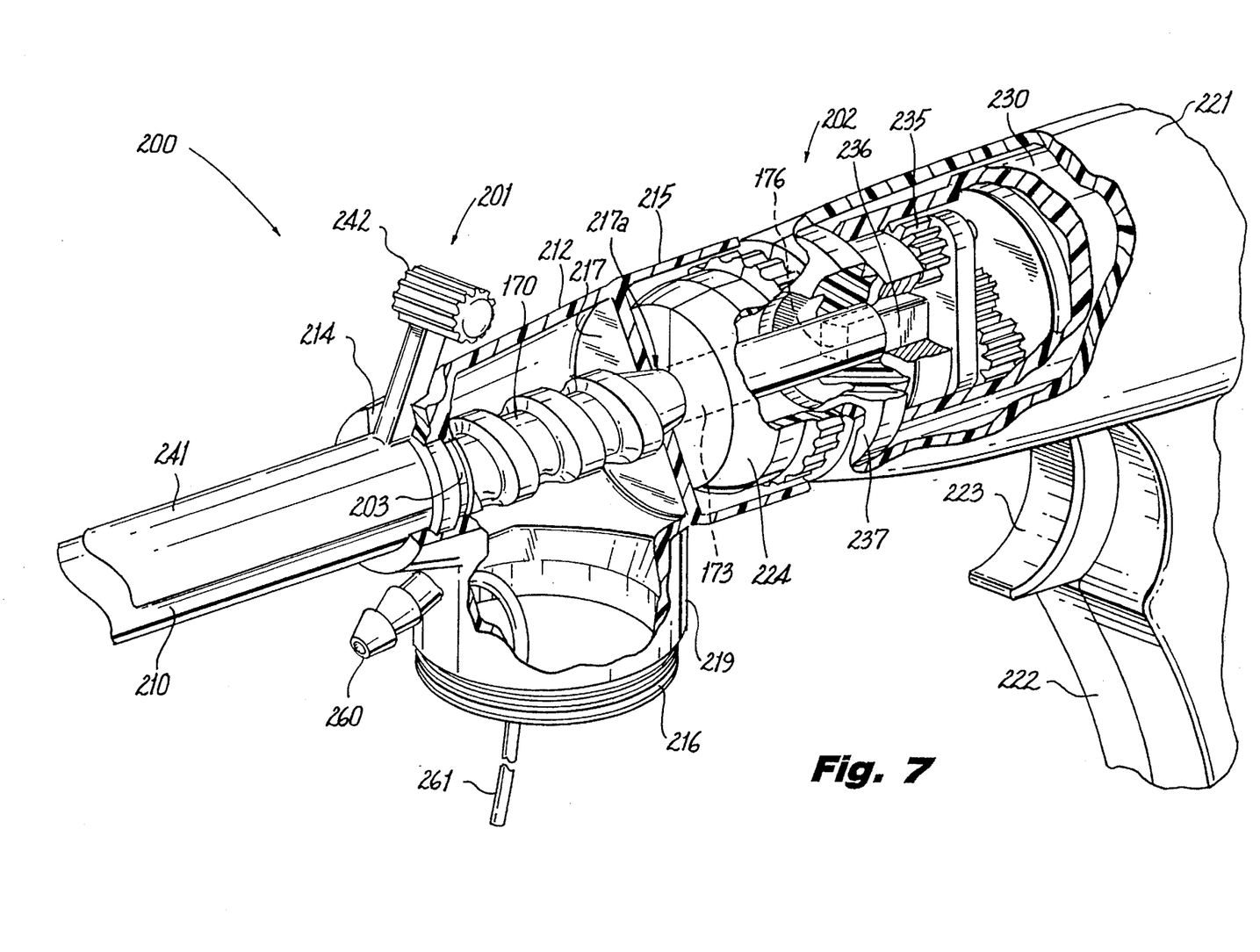
FIG. 7 is a partially cut away perspective of the endoscopic morcellator.

In addition to urging jaw actuator 241 distally, actuator lever 242 may be used to rotate the tubular member 210 along with cover flap 243 and jaw actuator 241. The proximal end of jaw actuator 241 is disposed within body portion 212 even when the actuator lever 242 is moved distally, thereby maintaining the jaw actuator 241 in slidable engagement with the body portion 212 and tubular member 210. The tubular member 210 is rotatably mounted to the body portion 212. Thus, by sliding the lever 242 out of slot 214 and moving lever 242 sideways the user can effect clockwise or counter-clockwise rotation of the endoscopic portion 201, thereby selectively reorienting access aperture 213, along with cover flap 243, in different lateral directions for reception of body tissue.

Referring again to FIGS. 4 to 6, the cover flap 243 is pivotably mounted to a connector member 246 which is attached to tubular member 210. Connector member 246 is disposed within a proximal slot 243a formed in cover flap 243 and is attached thereto by means of a pin 244 which extends through apertures 243c and 243d formed in cover flap 243 and aperture 246b formed in connector member 246. Cover flap 243 also includes a peg 243 which is abutted by opposing peg 211a on the tubular member 210 when the cover flap 243 is in the closed position. A helical expansion spring 245 is attached to both the cover flap 243 and the tubular member 210 and is circumferentially disposed around pegs 243b and 211a. Spring 245 resiliently biases the cover flap 243 to the closed position.

Pin 247 extends laterally through elongated slot 246a in the connector 246 and through apertures 241b and 241c in jaw actuator 241, thereby permitting jaw actuator 241 to slide longitudinally between a distal position and a proximal position without becoming disengaged from the apparatus. Jaw actuator 241 has a distal edge 241a which is inclined with respect to the longitudinal axis of the endoscopic portion 201.

As can be seen in FIGS. 5 and 6, as the jaw actuator 241 slides distally forward, the inclined distal edge 241a engages the proximal edge of the cover flap 243, moving the cover flap 243 to the open position against the biasing force of spring 245. When body tissue is positioned in aperture 213, the jaw actuator 241 can be pulled proximally backward, which allows spring 245 to bias the cover flap 243 closed, thereby urging the body tissue through aperture 213 and into contact with auger 170.

Figure 8:
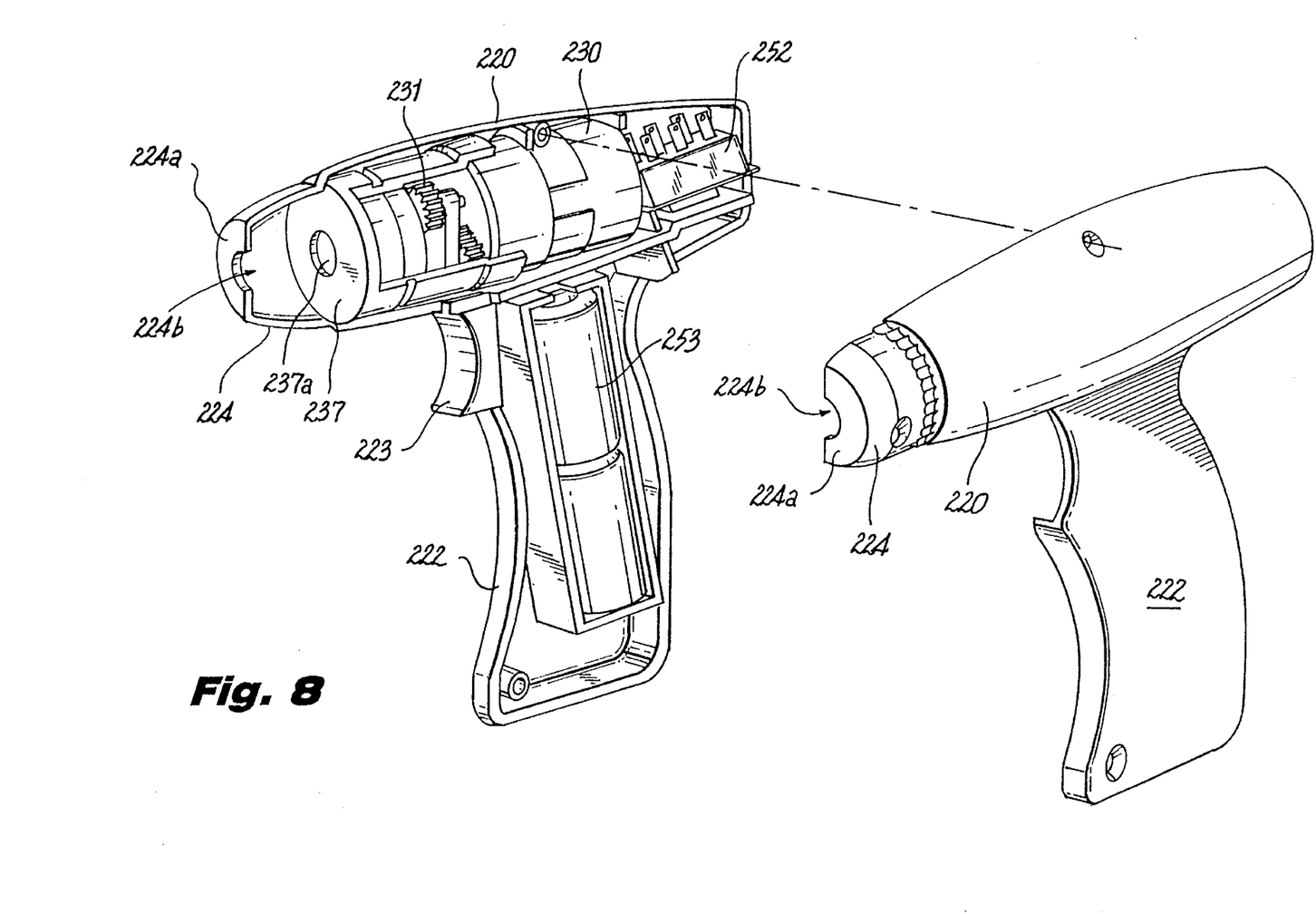
FIG. 8 is an exploded view of the housing section.

Referring now to FIGS. 1, 7, and 8, the body portion 212 can include a depending chamber 219 optionally having a threaded portion 216 for screw-on engagement of tissue container 250. Alternatively the tissue collection container 250 can include outward projections for engaging corresponding L-shaped notches in the depending chamber 219 to provide a bayonet type engagement. The tissue container 250 is preferably a transparent bottle resistant to fracture or breaking, and optionally fabricated from polycarbonate, acrylic, glass, or like material. A suction tube 261 includes an end which extends downwardly (as shown) into the container and another end which emerges from the apparatus at nozzle 260, which is ribbed for secure engagement to a vacuum hose. The vacuum hose (not shown) applies a vacuum to the tissue container 250 and the endoscopic portion 201 and the body portion 212 and draws the tissue and fluids into the aperture 213, through the tubular member 210, and auger 170, into the collection container 250, and out of the apparatus through the suction tube 261. Tissue which is not small enough to be drawn through the suction tube 261 remains in the tissue collection container 250.

The body portion 212 includes a rearward extension 215 which is adapted to engage the proximal nose portion 224 of the housing portion 202. As stated above, a bayonet type engagement feature 218, including outward projections formed on housing portion 202 for engaging corresponding L-shaped notches formed in the body portion 212, as shown in FIG. 1, can be used for releasable securing of the distal operating portion 201 to the handle portion 202. Body portion 212 further includes a back plate 217 which includes a sealed aperture 217a through which shaft 173 of the auger 170 is rotatably disposed. The seal, provided by, for example, close tolerances and/or sealing lubricants, helps to maintain the vacuum established in the distal operating portion, and prevents the exit of body fluids and tissue.

The housing portion 202, shown in FIGS. 7 and 8, includes a barrel portion 220 having a handle grip 222 with a battery pack 253 contained therein. A trigger 223 provides on-off control, and further has a setting to operate a double-pole double-throw switch 252 to effect reverse operation of the motor 230 in order to disengage any material which may become clogged within tubular member 210 during morcellation. The motor 230 is a conventional motor such as those commonly used for portable power tools such as hand drills. The transmission system 235 including gearing is likewise conventional. The motor and/or transmission are adapted for reversible operation. The power drive shaft 236, rotated by motor 230, is adapted to have a keyed fit into shaped aperture 176 to drive the auger 170. Bearing 237 has an aperture 237a through which shaft 173 is disposed. Likewise, nose portion 224 includes a front plate 224a having aperture 224b to accept shaft portion 173 of the auger 170.

Figure 9:
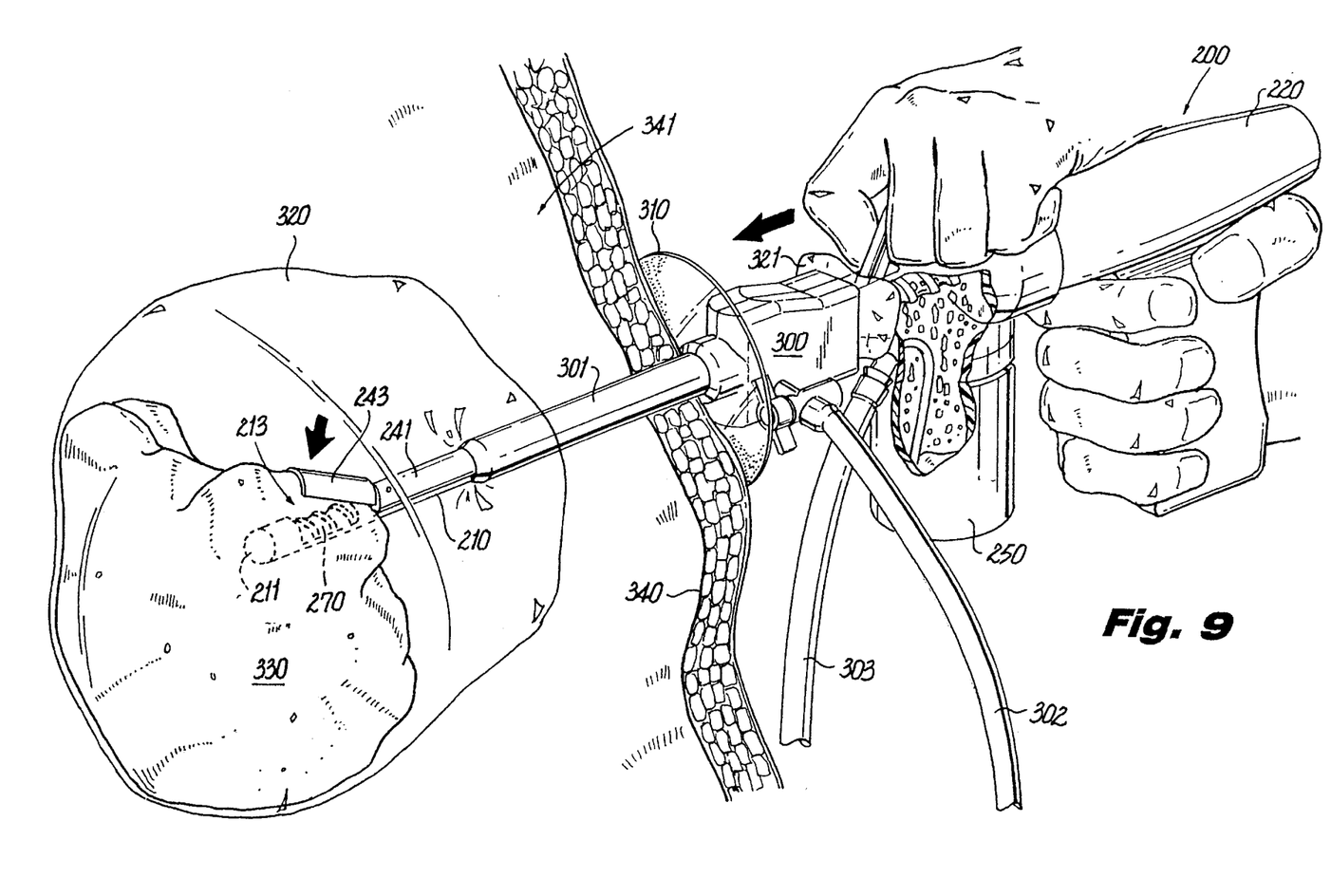
FIG. 9 is a perspective view illustrating use of the endoscopic morcellator in a surgical procedure.

Referring now to FIG. 9, operation of the morcellation apparatus 200 is illustrated wherein a cannula assembly 300 is shown with cannula portion 301 inserted through an incision in a wall of body tissue 340 and into an abdominal cavity 341 of a patient. The incision can be formed with conventional techniques using a trocar with a sharp tipped obturator. A patch 310 provides adhesion to the skin and more stable fixation of the endoscopic instrumentation deployed through cannula 301.

As shown in FIG. 9, a surgical bag 320 containing previously excised body tissue 330 is positioned in the abdomen with the mouth 321 of the bag 320 extending outside the cannula assembly 300. The elongated tubular member 210 of the endoscopic morcellizing apparatus 200 is disposed through cannula 301 and is positioned within the bag 320 with body tissue 330 in contact with auger 170 as described hereinabove. The cover flap 243 urges the tissue through aperture 213. In addition, cover flap 243 effectively shields the bag 320 from contact with the auger 170 as described hereinabove. A vacuum is applied via vacuum line 303 while insufflation of the abdominal cavity is maintained by pressure line 302. The user may optionally rotate the tubular member 210 by turning the lever 242 to one side or the other, thereby reorienting aperture 213.

Operation of trigger 223 controls on-off operation of the motor. If, for example, a piece of hard tissue or bone becomes entrapped by the auger, reversal of the rotation of the auger can be effectuated by trigger 223 as well to release the entrapped material.

In the embodiment of FIGS. 1 and 7, "grinding means" refers to auger 170. In the embodiment of FIGS. 1, 7, 8, and 9, "switch means responsive to user contact for actuating the rotary driver" refers to trigger 223. In the embodiment of FIGS. 7 and 8, "rotary driver means" refers to motor 230 and transmission 235. In the embodiment of FIG. 8, "switch for changing the direction of rotation of the auger" refers to switch 252.

Figure 10:
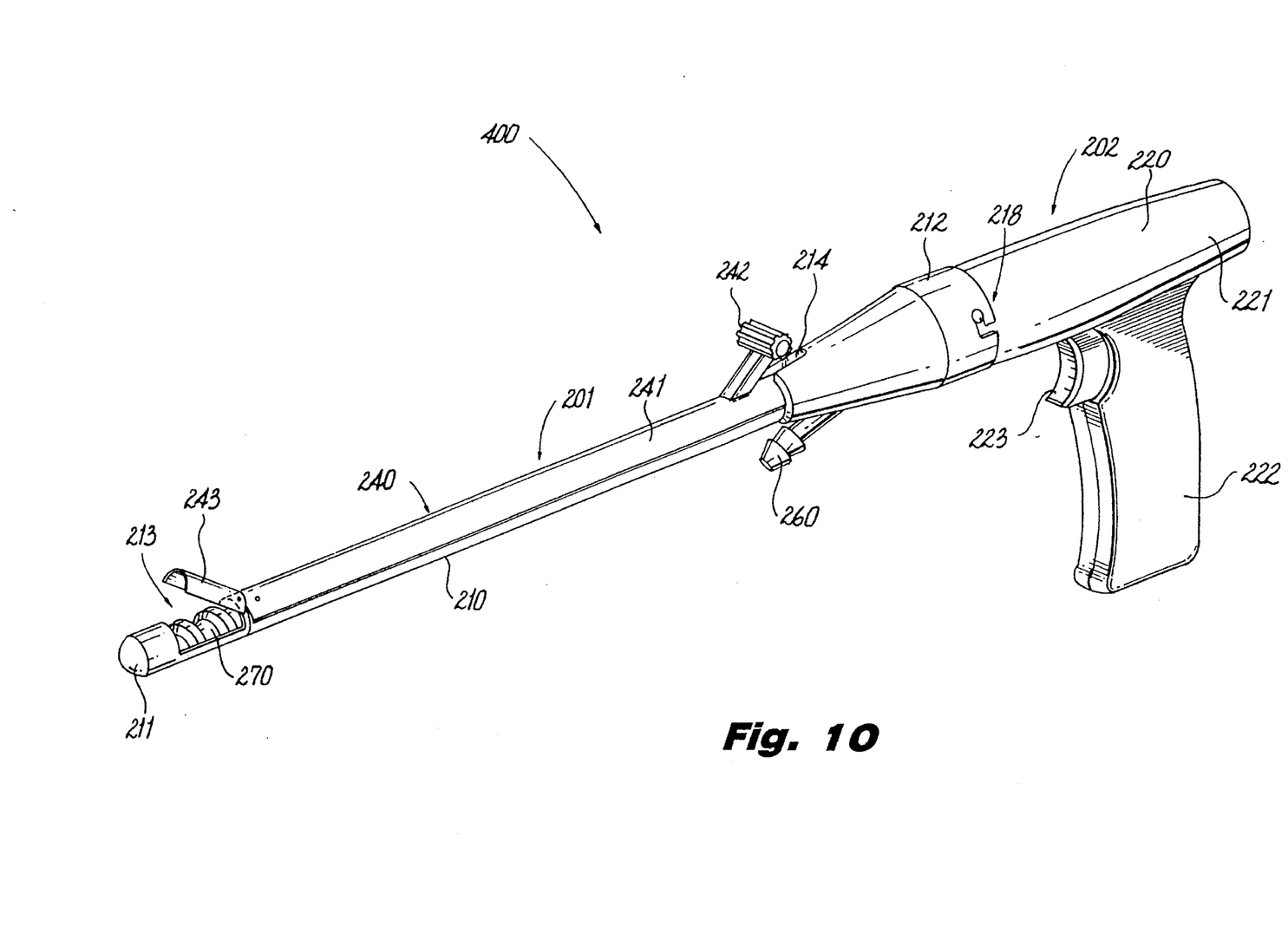
FIG. 10 is a perspective view of an alternative embodiment.

It will be understood that various modifications may be made to the embodiments disclosed herein. For example, referring to FIG. 10, an embodiment 400 of the apparatus is shown which is similar to apparatus 200, except that with embodiment 400 the collection of morcellized tissue can be effected within the body portion 212 without the use of a separate collection container such as container 250. In such an embodiment 400 the suction tube will be positioned within the interior of body portion 212 and will draw off morcellized tissue and fluid directly therefrom.

Therefore, the above description should not be construed as limiting, but merely as exemplifications of preferred embodiments. Those skilled in the art will envision many other possible variations that are within the scope and spirit of the claims appended hereto.

What is claimed is:

1. A surgical apparatus for morcellizing body tissue, which comprises:
    a) an endoscopic portion including an elongated tubular member having an axial bore, and an elongated auger rotatably disposed within the axial bore, the tubular member having an aperture which provides access for body tissue to contact the auger, and a cover member movable between a first position wherein the aperture is covered and a second position wherein the aperture is uncovered; and
    b) a housing portion engaged with the endoscopic portion and including a rotary driver mounted therein, the rotary driver being operatively associated with the auger, and an actuation member responsive to user contact for actuating the rotary driver, wherein actuation of the rotary driver causes rotation of the auger.

2. The surgical apparatus of claim 1 wherein said tubular member has a closed distal end and said aperture is laterally positioned on a side of the elongated tubular member spaced from the closed distal end.

3. The surgical apparatus of claim 1 wherein said auger comprises at least one land with a helical cutting edge.

4. The surgical apparatus of claim 1 wherein said tubular member is rotatable relative to the housing.

5. The surgical apparatus of claim 1 wherein said rotary driver includes a motor, a transmission, and switch for changing the direction of rotation of said auger.

6. The surgical apparatus of claim 1 wherein said endoscopic portion further includes a tissue collection container.

7. The surgical apparatus of claim 6 further including a suction tube having a first end positioned within tissue collection container and a second end positioned exterior to the apparatus.

8. The surgical apparatus of claim 6 further including means for removably attaching the tissue collection container to the endoscopic portion.

9. The surgical apparatus of claim 1 wherein said housing portion further includes at least one battery.

10. The surgical apparatus of claim 1 wherein said cover member is hingedly connected to the elongated member and pivotally movable between the first and second positions.

11. The surgical apparatus of claim 1 including an elongated cover member actuator extending parallel to the elongated tubular member and having an inclined distal edge for contacting a proximal edge of the cover member.

12. The apparatus of claim 11 wherein the elongated cover member actuator is slidable between a distal position and a proximal position, wherein the inclined distal edge of the elongated cover member actuator contacts the proximal edge of the cover member and causes said cover member to open in response to the movement of the cover member actuator to the distal position.

13. The apparatus of claim 1 wherein the cover member is hingedly connected to the tubular member.

14. The apparatus of claim 1 further comprising bayonet mounting means for releasably engaging the housing portion and the endoscopic portion.

15. A surgical apparatus for morcellizing body tissue, which comprises:
    a) an endoscopic portion including an elongated tubular member having an axial bore, and an elongated auger rotatably disposed within the axial bore, the tubular member having an aperture which provides access for body tissue to contact the auger, and a cover member movable between a first position wherein the aperture is covered and a second position wherein the aperture is uncovered, wherein the cover member is resiliently biased to the closed position by a resilient member; and
    a housing portion engaged with the endoscopic portion and including a rotary driver mounted therein, the rotary driver being operatively associated with the auger, and an actuation member responsive to user contact for actuating the rotary driver, wherein actuation of the rotary driver causes rotation of the auger.

16. A surgical apparatus for morcellizing body tissue, which comprises:
    a) an endoscopic portion including an elongated tubular member having an axial bore, and an elongated auger rotatably disposed within the axial bore, the tubular member having an aperture which provides access for body tissue to contact the auger, and a cover member movable between a first position wherein the aperture is covered and a second position wherein the aperture is uncovered, wherein said tubular member includes a plurality of longitudinally extending internal ribs, each rib having an inclined first side; and
    b) a housing portion engaged with the endoscopic, portion and including a rotary driver mounted therein, the rotary driver being operatively associated with the auger, and an actuation member responsive to user contact for actuating the rotary driver, wherein actuation of the rotary driver causes rotation of the auger.

17. A surgical apparatus for morcellizing body tissue, which comprises:
    a) an endoscopic portion including an elongated tubular member having an axial bore, a distal end portion and a proximal end portion, and an elongated grinding means rotatably disposed within the axial bore, the tubular member having an aperture which provides access for body tissue to contact said grinding means, and a cover member movable between a first position wherein the aperture is covered, and a second position wherein the aperture is uncovered, said cover member having a proximal end hinged to the tubular member; and b) a housing portion engaged with the proximal end portion of the endoscopic portion and having a rotary driver means mounted therein for driving the grinding means, and switch means responsive to user contact for actuating the rotary driver means.

18. The apparatus of claim 17 further comprising bayonet mounting means for releasably engaging the housing portion and the endoscopic portion.

19. A method for morcellizing body tissue, comprising:
a) providing a morcellizing apparatus which includes
  i) an endoscopic portion including an elongated tubular member having an axial bore, and an elongated auger rotatably disposed within the axial bore, the tubular member having a distal end and an aperture spaced apart from the distal end for providing access for body tissue to contact said auger, and a cover member movable between a first position wherein the aperture is covered and a second position wherein the aperture is uncovered, said cover member being biased to said first position by a resilient member, and
  ii) a housing portion engaged with the endoscopic portion and having a rotary driver mounted therein, and an actuation member responsive to user contact for actuating the rotary driver, wherein actuation of the rotary driver causes rotation of the auger;
b) forming an incision in a wall of body tissue;
c) inserting the distal end of the elongated tubular member through the incision;
d) positioning said cover member in said second position;
e) positioning the distal end of the tubular member such that the aperture is adjacent body tissue to be morcellized and at least a portion of the auger comes into contact with the body tissue to morcellized; and
f) rotating the auger such that the body tissue to be morcellized is drawn into the tubular member morcellized, while permitting said cover member to move from the second position to the first position in response to biasing force applied by said resilient member.

20. The method of claim 19 further comprising the step of inserting a cannula into the incision formed in the wall of body tissue, after forming said incision.

21. The method of claim 19 further comprising the steps of inserting a surgical bag through the incision, excising the body tissue to be morcellated, placing said excised body tissue into the surgical bag, and inserting the distal end of the elongated tubular member into said surgical bag, after forming the incision in the wall of body tissue.

22. The method of claim 19 wherein the morcellizing apparatus includes a container for collection of morcellized tissue, and said method further includes the step of collecting the morcellized tissue.

23. The method of claim 22 wherein the morcellizing apparatus includes a suction tube, and said step of collecting the morcellized tissue is accomplished by applying a vacuum to said container and suctioning the morcellized tissue.

24. The apparatus of claim 19 further comprising bayonet mounting means for releasably engaging the housing portion and the endoscopic portion.

* * * * *